United States Patent
Chiba et al.

(10) Patent No.: US 7,586,112 B2
(45) Date of Patent: Sep. 8, 2009

(54) PARTICLE THERAPY SYSTEM

(75) Inventors: Daishun Chiba, Hitachi (JP); Yasutake Fujishima, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 344 days.

(21) Appl. No.: 11/339,842

(22) Filed: Jan. 26, 2006

(65) Prior Publication Data

US 2007/0053484 A1    Mar. 8, 2007

Related U.S. Application Data

(63) Continuation of application No. 11/018,320, filed on Dec. 22, 2004, now abandoned.

(30) Foreign Application Priority Data

Dec. 26, 2003    (JP) ............................ 2003-433617

(51) Int. Cl.
*A61N 5/01* (2006.01)
(52) U.S. Cl. ............... 250/492.3; 250/492.1; 250/493.1
(58) Field of Classification Search .............. 250/492.3, 250/493.1
See application file for complete search history.

(56) References Cited

U.S. PATENT DOCUMENTS

| | | |
|---|---|---|
| 4,794,340 A | 12/1988 | Ogasawara |
| 5,363,008 A | 11/1994 | Hiramoto et al. |
| 5,585,642 A * | 12/1996 | Britton et al. ............ 250/492.3 |
| 5,682,414 A | 10/1997 | Saito |
| 5,895,926 A | 4/1999 | Britton et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0200982 A1 | 10/2004 | Moriyama et al. |

FOREIGN PATENT DOCUMENTS

JP    11-501232    2/1999

* cited by examiner

*Primary Examiner*—David A Vanore
(74) *Attorney, Agent, or Firm*—Dickstein Shapiro LLP

(57) ABSTRACT

A particle therapy system capable of increasing the number of patients treated in one treatment room per unit time. The particle therapy system comprises a charged particle beam generator for generating an ion beam, an irradiation apparatus for irradiating the ion beam extracted from the charged particle beam generator to an irradiation target, a beam transport system for transporting the ion beam extracted from the charged particle beam generator to the irradiation apparatus, and a central control unit for producing a set of command data to command excitation currents for magnets disposed in the charged particle beam generator and the beam transport system, the set of command data being classified into group-1 data and group-2 data.

14 Claims, 11 Drawing Sheets

FIG.4

PATIENT DATA

| PATIENT ID No. | IRRADIATION DOSE | (TREATMENT ROOM No.) | GANTRY ANGLE | ENERGY |
|---|---|---|---|---|
| 650098 | ... | (NO.1) | 0° | 70MeV |

FIG.5

GB : BENDING MAGNET
GQ : QUADRUPOLE MAGNET
GS : STEERING MAGNET

COMMON TO ALL TREATMENT ROOMS

| ENERGY (MeV) | BEFORE ACCELERATION | SYNCHROTRON | | AFTER ACCELERATION | |
|---|---|---|---|---|---|
| | GB10 | GQ9 | GB14 | GQ13 | GB17 | GQ18 |
| 70 | | | Pattern 70 | | | |
| 80 | ... | ... | Pattern 80 | ... | ... | ... |
| 90 | | | Pattern 90 | | | |

— Gr.1 —

FIRST TREATMENT ROOM 2A | BETWEEN BRANCHES | SECOND TREATMENT ROOM 2B | BETWEEN BRANCHES

| ENERGY (MeV) | GQ22A | GQ24A | GS7HA | GS7VA | GS8HA | GS8VA | GQ19 | GQ22B | GQ24B | GS7HB | GS7VB | GS8HB | GS8VB | GQ20 |
|---|---|---|---|---|---|---|---|---|---|---|---|---|---|---|
| 70 | | | | | | | | | | | | | | |
| 80 | ... | ... | ... | ... | ... | ... | ... | ... | ... | ... | ... | ... | ... | ... |
| 90 | | | | | | | | | | | | | | |

— Gr.2 — Gr.1 — Gr.2 — Gr.1 —

THIRD TREATMENT ROOM 2C | BETWEEN BRANCHES | FOURTH TREATMENT ROOM 3

| ENERGY (MeV) | GQ22C | GQ24C | GS7HC | GS7VC | GS8HC | GS8VC | GQ27 | GQ28 |
|---|---|---|---|---|---|---|---|---|
| 70 | | | | | | | | |
| 80 | ... | ... | ... | ... | ... | ... | ... | ... |
| 90 | | | | | | | | |

| SWITCHING POWER SUPPLY 162-1 | SWITCHING POWER SUPPLY 162-2 | SWITCHING POWER SUPPLY 162-3 | SWITCHING POWER SUPPLY 162-4 |
|---|---|---|---|
| ... | ... | ... | ... |
| ... | ... | ... | ... |

CONTROL COMMAND DATA INDEX

| FILE NAME | | WRITTEN BY | |
| ENERGY | Mev | APPROVED BY | |

COURSE   1 ○   2 ○   3 ○   4 ○

BEAM INTENSITY [ ] %

GANTRY ANGLE [ ] DEGREES

COURSE : 1COURCE
BEAM STRENGTH : 100 %

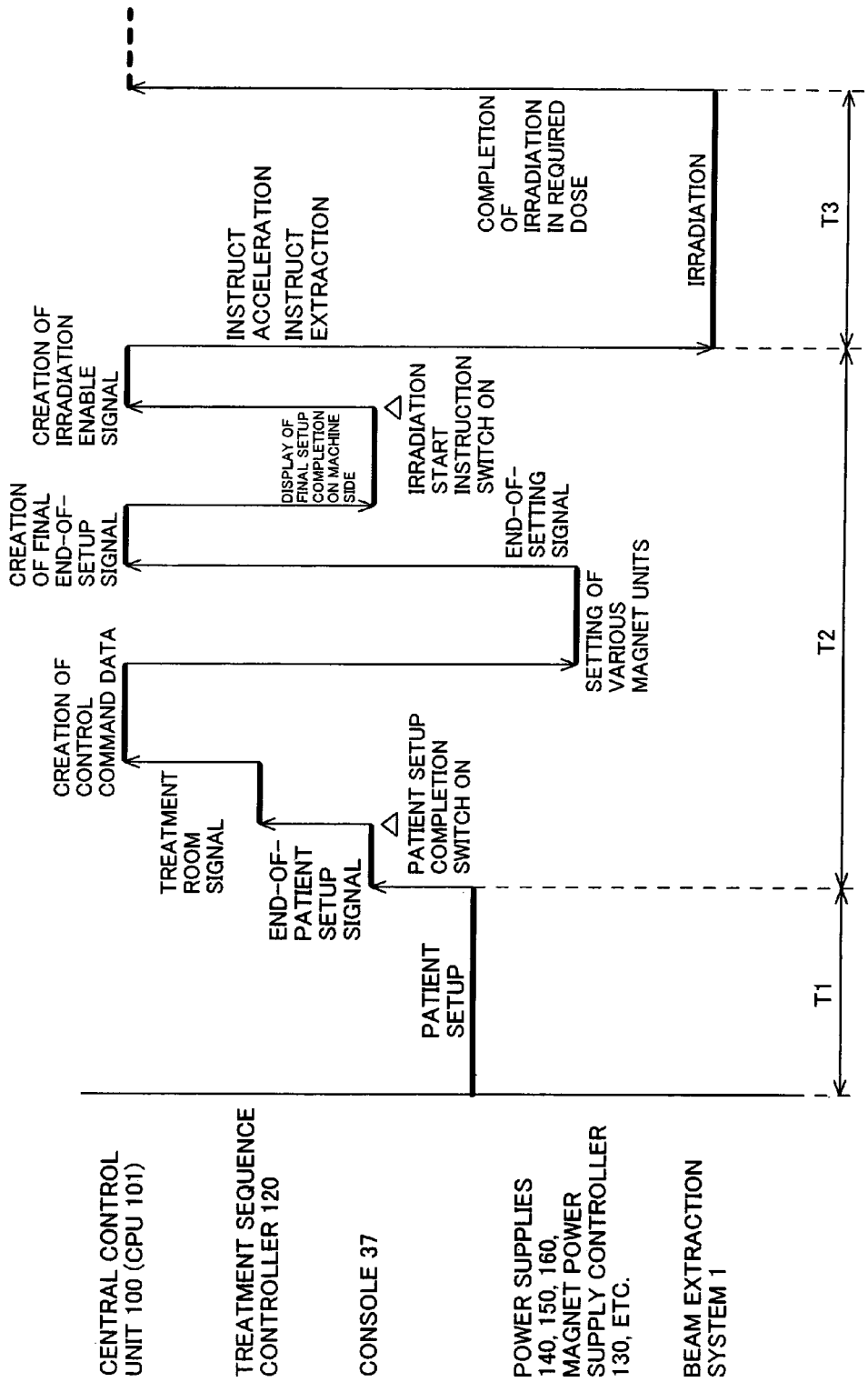

PARTICLE THERAPY SYSTEM

This application is a continuation of U.S. patent application Ser. No. 11/018,320, filed on Dec. 22, 2004, now abandoned, the entire disclosure of which is incorporated by reference herein.

BACKGROUND OF THE INVENTION

1. Field of the Invention

The present invention relates to a particle therapy system, and more particularly to a particle therapy system for irradiating a charged particle beam, such as a proton or carbon ion beam, to a diseased part for treatment.

2. Description of the Related Art

There is known a therapy method of irradiating a charged particle beam, such as a proton beam, to a diseased part, e.g., a cancer, in the body of a patient. A large-scaled one of therapy systems used for practicing such a therapy method conventionally comprises a charged particle beam generator, a beam transport system, and a plurality of treatment rooms. The charged particle beam accelerated by the charged particle beam generator reaches an irradiation apparatus in each treatment room through the beam transport system, and it is irradiated to the diseased part in the patient body from a nozzle of the irradiation apparatus. For that purpose, the beam transport system comprises a first beam transport system as one common system and a plurality of beam transport systems branched from the one first beam transport system and led to the respective irradiation apparatuses in the plurality of treatment rooms. At a position where each of the branched beam transport systems is branched, a switching magnet is disposed to bend the charged particle beam from the first beam transport system to be introduced to the corresponding branched beam transport system (see, e.g., Patent Reference 1: JP,A 11-501232 (pp. 12-13, FIGS. 1 and 2).

SUMMARY OF THE INVENTION

Generally, a therapy system having a plurality of treatment rooms is operated by repeating each cycle comprising the steps of performing a setup in each treatment room, such as positioning of a patient, outputting a command value signal from a control unit to each of magnets disposed in a charged particle beam generator and a beam transport system when the beam is requested from the treatment room (or treatment control room) in which the setup has completed, to thereby perform beam setting and form a beam transport path led to the relevant treatment room, and irradiating the beam to the patient. During a period in which the beam setting and irradiation are performed in one treatment room, a next treatment room completes a setup and comes into a standby state. Therefore, as soon as the irradiation has completed in one treatment room, the beam setting and the formation of the beam transport path for the next treatment room can be performed at once. This means that if the beam setting takes a long time, a standby time is prolonged and treatment efficiency lowers. For that reason, a beam setting time is preferably as short as possible.

In the known particle therapy system, though not specifically described in the above-cited Patent Reference 1, it is usual that various command values (hereinafter referred to as a "command value group") outputted from the control unit to the respective magnets are simply stored in entirety, as they are, for each beam type. The term "beam type" used herein represents each type of beam defined in accordance with parameters, such as beam energy, intensity, a beam extraction destination (e.g., treatment room No.), and an angle of a rotating gantry. As a recent tendency, the number of types of required beams increases with a more variety of tumors. Assuming that the parameters for defining the beam types include, for example, 400 levels of energy, 10 levels of intensity, 4 kinds of beam extraction destinations (i.e., four treatment rooms), and 720 rotation angles of a rotating gantry (corresponding to 360 angles in units of 0.5 degree), 400×10×4×720=11,520,000 kinds of command value groups must be stored in total.

The necessity of handling such a very large number of command value groups accompanies with a problem as follows. In the beam setting step, the control unit takes a relatively long time to search for, from among the very large number of command value groups, a particular command value group corresponding to the beam requested from the treatment room, and hence a time required for the beam setting is prolonged. Accordingly, treatment efficiency lowers and the number of patients treated in each treatment room per unit time reduces.

With the view of overcoming the problems in the related art, it is an object of the present invention to provide a particle therapy system capable of increasing the number of patients treated in one treatment room per unit time.

To achieve the above object, one feature of the present invention resides in producing a group of command values to command excitation currents for magnets disposed in a charged particle beam generator and a beam transport system for transporting a charged particle beam extracted from the charged particle beam generator to an irradiation apparatus, the group of command values being classified into a first command value group and a second command value group. With this feature, by employing the second command value group to command the excitation currents for steering magnets disposed in a gantry transport system and employing the first command value group to command the excitation currents for other magnets, for example, the first command value group in the whole of the command value group can be used in common when only a rotating gantry angle among parameters specifying the beam type is different, because the first command value group does not depend on the rotating gantry angle. Accordingly, the number of the command value groups to be stored can be greatly reduced in comparison with the known system in which the command value groups for the respective magnets are all simply stored as they are, and a search time required for specifying the necessary command value group from among the stored command value groups can be cut. As a result, it is possible to shorten a beam setting time in a control unit, and to increase the number of patients treated in one treatment room per unit time.

Another feature of the present invention resides in further comprising an angle development computing unit for computing the second command value group depending on the rotation angle of the rotating gantry. With this feature, when the operator prepares one command value group at a certain level of beam energy, for example, by adjusting command values while actually irradiating the charged particle beam at a certain rotating gantry angle, the second command value group corresponding to the other rotating gantry angles (in units of, e.g., 0.5 degree) at that beam energy level can be automatically computed based on the command value group prepared through the adjustment. By computing and preparing the command value groups depending on the rotating gantry angle in such a way, whatever rotating gantry angle is requested from the treatment room, the beam transport system can be set up in response to the request, and hence a beam automatically settable range of the control unit can be greatly enlarged.

Still another feature of the present invention resides in further comprising an energy development computing unit for computing the first and second command value groups depending on energy of the charged particle beam extracted from the charged particle beam generator. With this feature, when an operator prepares one command value group at a certain rotating gantry angle, for example, by adjusting common values while actually irradiating the charged particle beam at a certain level of beam energy, the first and second command value groups corresponding to the other levels of beam energy (in units of, e.g., 0.5 MeV) at that rotating gantry angle can be automatically computed based on the command value group prepared through the adjustment. By computing and preparing the command value groups depending on the beam energy in such a way, whatever beam energy is requested from the treatment room, the beam transport system can be set up in response to the request, and hence a beam automatically settable range of the control unit can be greatly enlarged.

Still another feature of the present invention resides in further comprising an index information storing unit for storing index information to make the first command value group and the second command value group correspondent to each other, and a reading unit for reading the first command value group and the second command value group, which are made correspondent to each other, by using the index information. With this feature, the operator can specify the required command value group by using only the index information without being aware of the fact that the command value groups are classified into two groups, and convenience in handling of data can be improved. Further, the first command value group and the second command value group can be avoided from being read in a false combination.

Thus, according to the present invention, the number of patients treated in each treatment room per unit time can be increased.

BRIEF DESCRIPTION OF THE DRAWINGS

FIG. 4 is a table showing one example of treatment planning data per patient;

FIG. 5 shows a power supply control table previously stored in a disk disposed in a central control unit;

FIG. 7 is an illustration showing one example of index data displayed on a console display;

FIG. 11 a time chart showing a flow of the operation and control over time in the particle therapy system according to one embodiment.

DESCRIPTION OF THE PREFERRED EMBODIMENTS

A particle therapy system, as one preferable embodiment of the present invention, will be described below with reference to the drawings.

Figure 1:
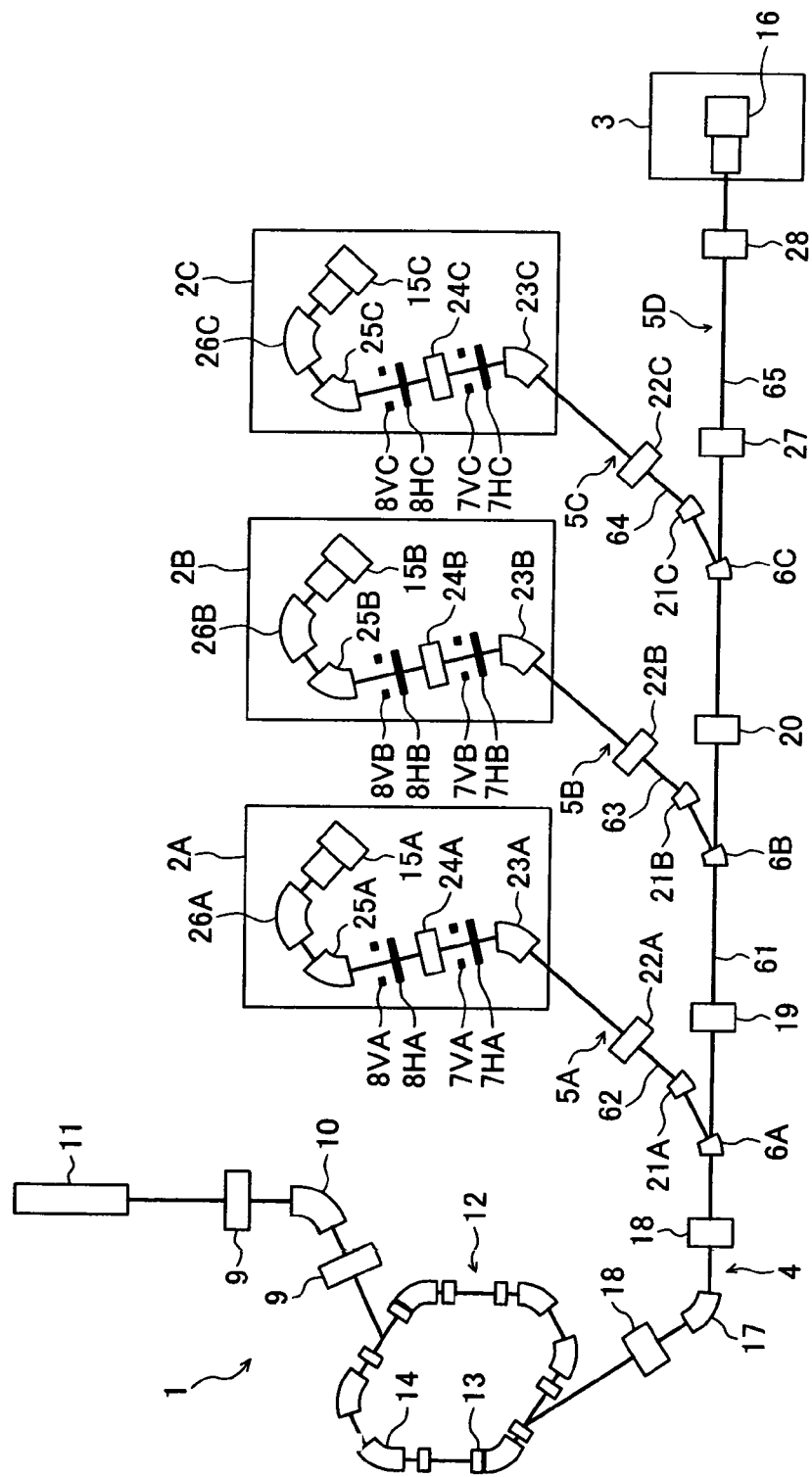
FIG. 1 is a conceptual diagram showing an overall schematic construction of a particle therapy system according to one embodiment of the present invention.

As shown in FIG. 1, a particle therapy system of this embodiment comprises a charged particle beam generator 1, four treatment rooms 2A, 2B, 2C and 3, a beam transport system made up of a first beam transport system (beam transport system in claims) 4 connected to the downstream side of the charged particle beam generator 1 and second beam transport systems (beam transport system in claims) 5A, 5B, 5C and 5D branched from the first beam transport system 4, and switching magnets 6A, 6B and 6C. The first beam transport system 4 serves as a common beam transport system for introducing an ion beam to each of the second beam transport systems 5A, 5B, 5C and 5D.

The charged particle beam generator 1 comprises an ion source (not shown), a pre-stage charged particle beam generator (linac) 11, and a synchrotron 12. Ions (e.g., proton or carbon ions) generated from the ion source are accelerated by the pre-stage charged particle beam generator (e.g., a linear charged particle beam generator) 11. An ion beam (proton beam) emitted from the pre-stage charged particle beam generator 11 enters the synchrotron 12 through quadrupole magnets 9 and a bending magnet 10. The ion beam in the form of a charged particle beam (corpuscular beam) is accelerated in the synchrotron 12 in which energy is given to the ion beam with radio-frequency (RF) power applied from an RF cavity (not shown). After energy of the ion beam circulating in the synchrotron 12 has been increased up to a setting level (e.g., 100 to 200 MeV), an RF wave is applied to the circulating ion beam from an RF knockout electrode (not shown) for beam extraction. With the application of the RF wave, the ion beam circulating within a separatrix is forced to transit to the outside of the separatrix and to exit from the synchrotron 12 through a beam extraction deflector (not shown). At the time of extracting the ion beam, currents supplied to magnets, such as quadrupole magnets 13 and bending magnets 14, disposed in the synchrotron 12 are held at setting values, and therefore the separatrix is also held substantially constant. The extraction of the ion beam from the synchrotron 12 is stopped by ceasing the application of the RF power to the RF knockout electrode.

The ion beam extracted from the synchrotron 12 is transported to the downstream side through the first beam transport system 4. The first beam transport system 4 has a beam line 61 and includes a quadrupole magnet 18, a bending magnet 17, another quadrupole magnet 18, a switching magnet 6A, a quadrupole magnet 19, a switching magnet 6B, a quadrupole magnet 20, and a switching magnet 6C which are successively arranged on the beam line 61 in this order from the upstream side in the direction of beam advance. The ion beam introduced to the first beam transport system 4 is selectively introduced to one of the second beam transport systems 5A, 5B, 5C and 5D depending on the presence or absence of a bending action provided in accordance with switching between excitation and non-excitation of those quadrupole and bending magnets and the switching magnets 6A, 6B and 6C. Each of the switching magnets is one type of bending magnet.

The second beam transport system 5A has a beam line 62 connected at one end to the beam line 61 and at the other end to an irradiation apparatus 15A disposed within the treatment room 2A, and it includes a bending magnet 21A, a quadrupole magnet 22A, a bending magnet 23A, a steering magnet 7HA, a steering magnet 7VA, a quadrupole magnet 24A, a steering magnet 8HA, a steering magnet 8VA, a bending magnet 25A, and a bending magnet 26A which are successively arranged on the beam line 62 in this order from the upstream side in the direction of beam advance. The steering magnets 7HA, 7VA, 8HA and 8VA are magnets for adjusting the position of the ion beam. Among them, the steering magnets 7HA, 8HA adjust the position of the ion beam in the horizontal direction, while the steering magnets 7VA, 8VA adjust the position of the ion beam in the vertical direction. The steering magnets 7HA, 7VA, 8HA and 8VA are disposed in a part (gantry transport system) of the second beam transport system 5A which locates within the treatment room 2A.

The second beam transport system 5B has a beam line 63 connected at one end to the beam line 61 and at the other end to an irradiation apparatus 15B disposed within the treatment room 2B, and it includes a bending magnet 21B, a quadrupole magnet 22B, a bending magnet 23B, a steering magnet 7HB, a steering magnet 7VB, a quadrupole magnet 24B, a steering magnet 8HB, a steering magnet 8VB, a bending magnet 25B, and a bending magnet 26B which are successively arranged on the beam line 63 in this order from the upstream side in the direction of beam advance. The steering magnets 7HB, 7VB, 8HB and 8VB are similar to the steering magnets 7HA, 7VA, 8HA and 8VA in the second beam transport system 5A.

The second beam transport system 5C has a beam line 64 connected at one end to the beam line 61 and at the other end to an irradiation apparatus 15C disposed within the treatment room 2C, and it includes a bending magnet 21C, a quadrupole magnet 22C, a bending magnet 23C, a steering magnet 7HC, a steering magnet 7VC, a quadrupole magnet 24C, a steering magnet 8HC, a steering magnet 8VC, a bending magnet 25C, and a bending magnet 26C which are successively arranged on the beam line 64 in this order from the upstream side in the direction of beam advance. The steering magnets 7HC, 7VC, 8HC and 8VC are similar to the steering magnets 7HA, 7VA, 8HA and 8VA in the second beam transport system 5A.

The second beam transport system 5D has a beam line 65 connected at one end to the beam line 61 and at the other end to a fixed irradiation apparatus 16 disposed within the treatment room 3, and it includes quadrupole magnets 27, 28 which are successively arranged on the beam line 65 in this order from the upstream side in the direction of beam advance.

With the arrangement described above, the ion beam introduced to the second beam transport system 5A is transported to the irradiation apparatus 15A through the beam line 62 with excitation of the corresponding magnets. The ion beam introduced to the second beam transport system 5B is transported to the irradiation apparatus 15B through the beam line 63 with excitation of the corresponding magnets. The ion beam introduced to the second beam transport system 5C is transported to the irradiation apparatus 15C through the beam line 64 with excitation of the corresponding magnets. Also, the ion beam introduced to the second beam transport system 5D is transported to the irradiation apparatus 16 through the beam line 65 with excitation of the corresponding magnets.

The treatment rooms 2A to 2C include respectively the irradiation apparatuses 15A to 15C each mounted to a rotating gantry (not shown) installed in the corresponding treatment room. The treatment rooms 2A to 2C are employed as, e.g., first to third treatment rooms for cancer patients, and the treatment room 3 is employed as a fourth treatment room for ocular treatment, which includes the fixed irradiation apparatus 16.

Figure 2:
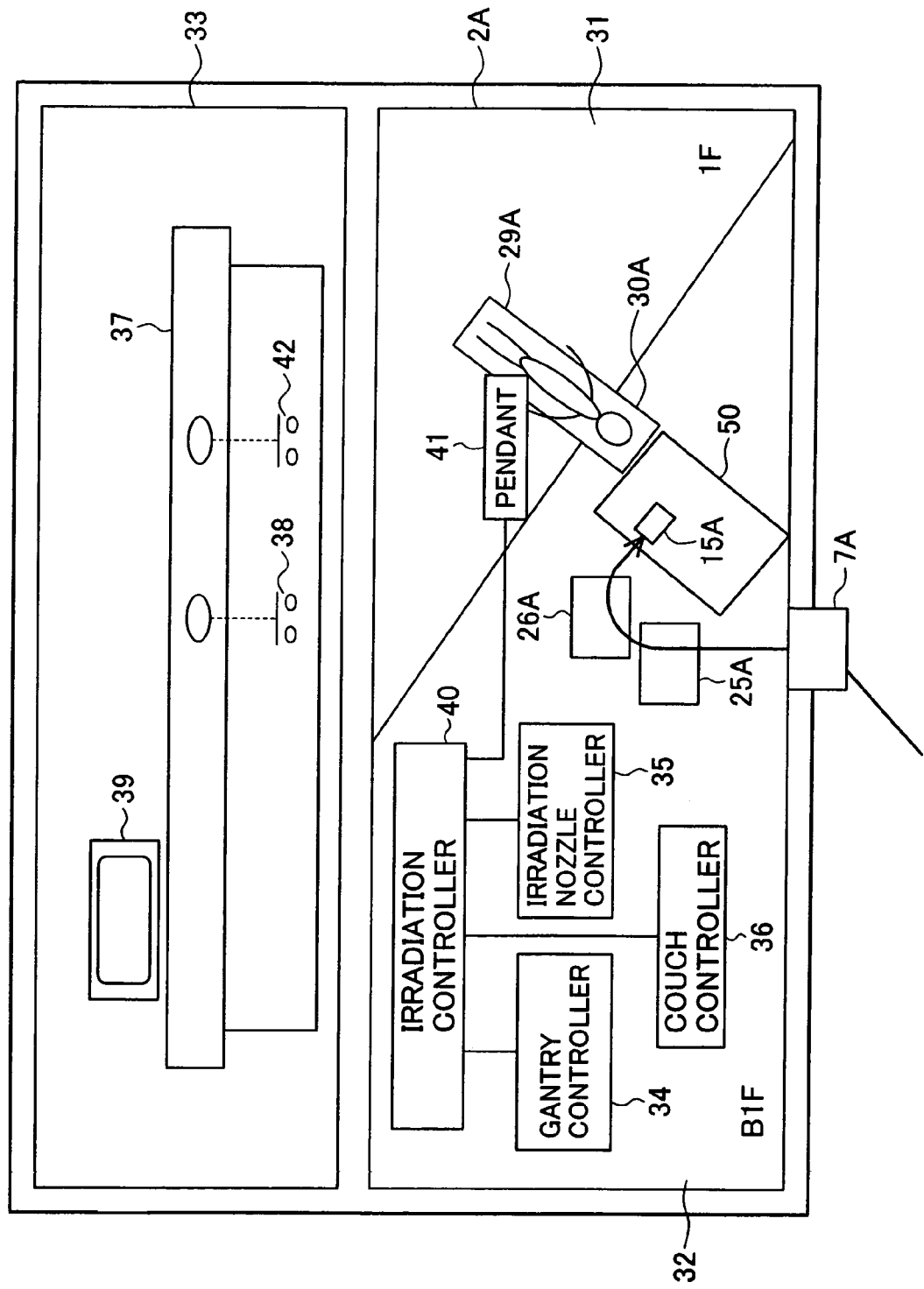
FIG. 2 is a conceptual plan view showing a detailed construction of one of treatment rooms shown in FIG. 1.

The construction and equipment layout in the treatment room 2A will be described below with reference to FIG. 2. Note that since the treatment rooms 2B, 2C also have the same construction and equipment layout as those in the treatment room 2A, a description thereof is omitted here. The treatment room 2A comprises a medical treatment room (compartment) 31 formed in the first floor, and a gantry room (compartment) 32 formed at a one step lower level, i.e., in the first basement. Further, an irradiation control room 33 is formed outside the treatment room 2A in an adjacent relation to it. The irradiation control room 33 is similarly formed with respect to each of the treatment rooms 2B and 2C. The irradiation control room 33 is isolated from both the medical treatment room 31 and the gantry room 32. However, the condition of a patient 30A in the medical treatment room 31 can be observed, for example, with a monitoring image taken by a TV camera (not shown) disposed in the medical treatment room 31.

An inverted U-shaped beam transport subsystem as a part of the second beam transport system 5A and the irradiation apparatus 15A are mounted to a substantially cylindrical rotating drum 50 of the rotating gantry (not shown). The rotating drum 50 is rotatable by a motor (not shown). A treatment gauge (not shown) is formed inside the rotating drum 50.

The irradiation apparatus 15A comprises a casing (not shown) mounted to the rotating drum 50 and connected to the inverted U-shaped beam transport subsystem, and a snout (not shown) provided at the fore end of a nozzle through which the ion beam exits. The casing and the snout include, though not shown, a bending magnet, a scatterer device, a ring collimator, a patient collimator, a bolus (compensator), etc., which are arranged therein.

The ion beam introduced to the irradiation apparatus 15A in the treatment room 2A from the inverted U-shaped beam transport subsystem through the beam line 62 has an irradiation field that is roughly collimated by the ring collimator in the irradiation apparatus 15A and is shaped by the patient collimator in match with the shape of a diseased part in the planar direction perpendicular to the direction of beam advance. Further, the ion beam has a penetration depth that is adjusted by the bolus in match with the maximum depth of the diseased part in the body of the patient 30A lying on a treatment couch 29A. Prior to irradiating the ion beam from the irradiation apparatus 15A, the treatment couch 29A is moved by a couch driver (not shown) to enter the treatment gauge, and is precisely positioned in place for the start of irradiation from the irradiation apparatus 15A. The ion beam thus formed by the irradiation apparatus 15A so as to have a dose distribution optimum for particle therapy is irradiated to the diseased part (e.g., an area where a tumor or a cancer grows; hereinafter referred to as a "tumor") in the body of the patient 30A. The energy of the irradiated ion beam is released in the tumor to form a high dose region. The travel of the ion beam in each of the other irradiation apparatuses 15B, 15C and the positioning of the treatment couch are performed in a similar manner to those in the irradiation unit 15A.

In this respect, the rotating drum 50 is rotated by controlling the motor rotation by a gantry controller 34. Also, the operation (energization) of the bending magnet, the scatterer device, the ring collimator, etc. in each of the irradiation apparatuses 15A to 15C is controlled by an irradiation nozzle controller 35. Further, the operation of the couch driver is controlled by a couch controller 36. These controllers 34, 35 and 36 are all controlled by an irradiation controller 40 disposed in the gantry room 32 inside the treatment room 2A. A pendant 41 is connected to the irradiation controller 40 through a cable extended to the side of the medical treatment room 31, and a doctor (or an operator) standing near the patient 30A transmits a control start signal and a control stop signal to the controllers 34 to 36 through the irradiation controller 40 by manipulating the pendant 41. For example, when the control start signal for the rotating gantry is outputted from the pendant 41, a central control unit 100 (described later) takes in angle information of the rotating gantry regarding the patient 30A from treatment planning information stored in a storage 110 and transmits the angle information to the corresponding gantry controller 34 through the irradiation controller 40. The gantry controller 34 rotates the rotating gantry based on the gantry angle information.

An operator console 37 disposed in the irradiation control room 33 includes a setup option switch 38 depressed by the operator when required setups, such as positioning of the treatment couch 29A, angle adjustment of the rotating gantry, and settings of various devices in the irradiation apparatus 15A, have completed, a display 39 for presenting display of a setup completion state on the mechanical side and index display (described later in detail), and an irradiation instruction switch 42 depressed by the operator at the time of starting the beam irradiation. The irradiation control room 33 is likewise arranged for the treatment room 3 separately.

Figure 3:
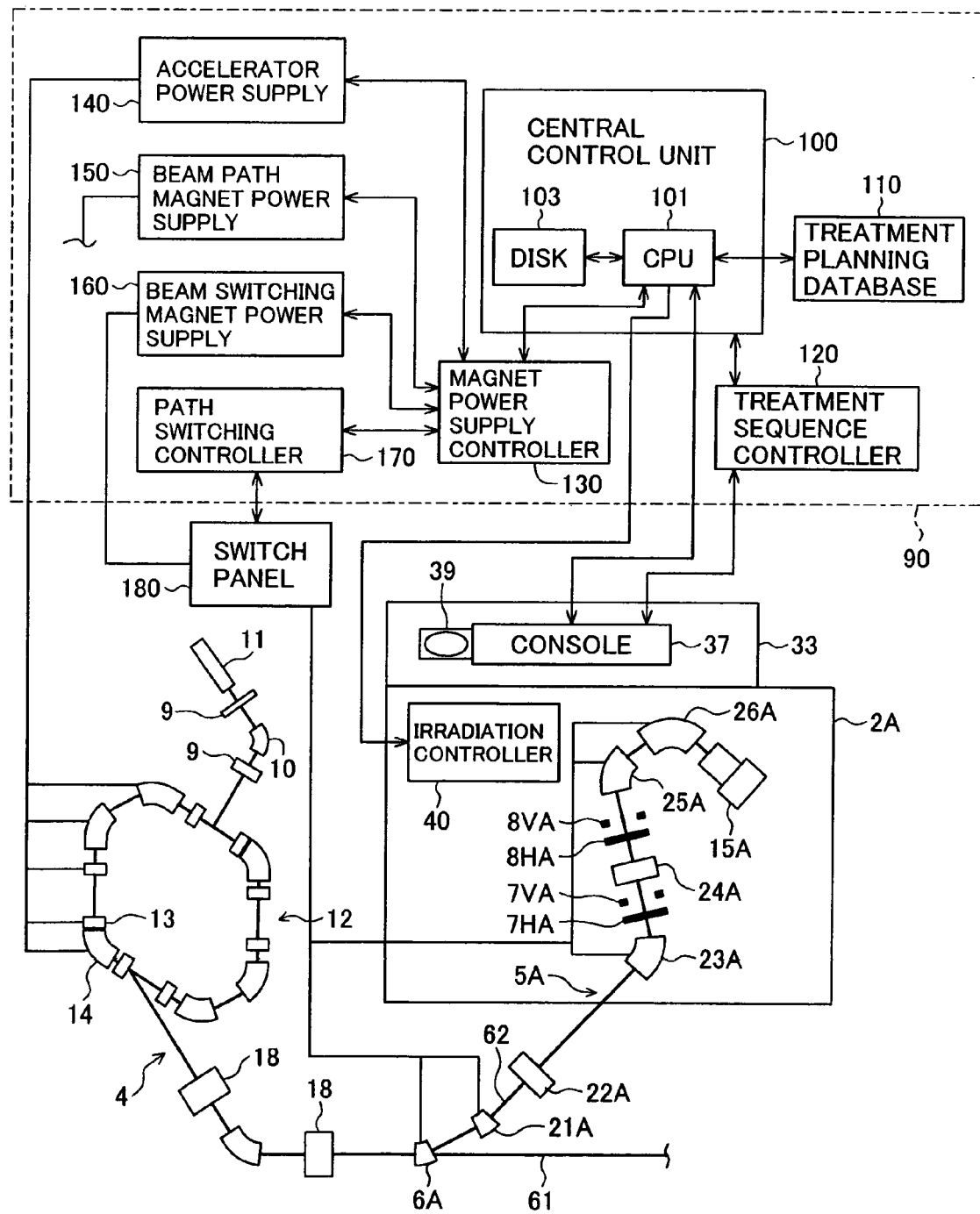
FIG. 3 is a block diagram showing a control system in the particle therapy system according to one embodiment of the present invention.

A control system incorporated in the particle therapy system of this embodiment will be described below with reference to FIG. 3. A control system 90 comprises a central control unit ("control unit" in claims) 100, a storage 110 storing a treatment planning database, a treatment sequence controller 120, a magnet power supply controller 130, a power supply unit for the accelerator (hereinafter referred to as an "accelerator power supply") 140, a power supply unit for the beam path magnets (hereinafter referred to as a "beam path power supply") 150, a power supply unit for the beam switching magnets (hereinafter referred to as an "beam switching power supply") 160, and a path switching controller 170. Further, the particle therapy system of this embodiment includes a switch panel 180. Note that, although the construction of only one 2A of the treatment rooms 2A to 2C is shown in FIG. 3 for the sake of simplicity of the drawing, the other two treatment rooms 2B, 2C are also similarly constructed.

The treatment planning database stored in the storage 110 records and accumulates therein treatment planning data which has been prepared by doctors in advance for all the patients who will receive the irradiation treatment. One example of the treatment planning data (patient data) stored in the storage 110 for each patient will be described with reference to FIG. 4. The treatment planning data contains the patient ID number, irradiation dose (per one shot), irradiation energy, gantry angle, irradiation field size (not shown), irradiation position (not shown), etc. Although the treatment planning data contains the beam energy in the illustrated example, the beam energy may be calculated in the central control unit 100 based on, e.g., range information because is the range information also contained in the treatment planning data.

A CPU 101 in the central control unit 100 reads, from the storage 110, the treatment planning data regarding the patient who is going to take the irradiation treatment. Among the thus-read treatment planning data, the necessary data (such as the gantry angle, the irradiation field size, and the irradiation position) is outputted to the respective controllers (i.e., the gantry controller 34, the irradiation nozzle controller 35, and the couch controller 36) via the irradiation controller 40. Responsively, the gantry controller 34 rotates the rotating gantry in accordance with the gantry angle information in the treatment planning data. The irradiation nozzle controller 35 performs settings of the bending magnet, the scatterer device, the ring collimator, etc. in the irradiation apparatus 15A in accordance with the irradiation field size information, etc. in the treatment planning data. Further, the couch controller 36 performs positioning of the treatment couch 29A in accordance with the irradiation position information in the treatment planning data.

When the patient comes into a state ready for the irradiation of the ion beam upon the completion of setups required prior to the irradiation, the operator goes out of the treatment room 2A, enters the corresponding irradiation control room 33, and depresses the setup completion switch (or button) 38 on the operator console 37. With the depression of the setup completion switch 38, a patient ready signal is generated and outputted to the treatment sequence controller 120.

The treatment sequence controller 120 sets the sequence of treatments to be performed in the treatment rooms 2A, 2B, 2C and 3. The treatment sequence for the respective treatment rooms is decided in accordance with the sequence in which the patient ready signals have been inputted from the setup completion switches 38 in the irradiation control rooms 33 corresponding to the treatment rooms 2A-2C and 3. The treatment room number having the top priority selected by the treatment sequence controller 120 (i.e., the number of the treatment room selected to start the irradiation therein at that time) is inputted to the CPU 101 in the central control unit 100. For convenience of the following description, that treatment room number is assumed here to be "No. 1". In other words, the treatment room 2A is assumed to be the selected treatment room.

Based on both the selected treatment room number (i.e., beam course information) and the parameters (such as the irradiation energy, the irradiation dose, and the gantry angle) contained in the treatment planning data and required for specifying the beam, the CPU 101 creates control command data (command value group) for supply of excitation power to the respective magnets from a power supply control table that is previously stored in the disk 103 (e.g., a hard disk or a CD-ROM) disposed in the central control unit 100. One example of the power supply control table will now be described with reference to FIG. 5. As shown in FIG. 5, corresponding to respective values (70, 80, 90, . . . [MeV] in the illustrated example) of the irradiation energy, various parameters are preset which include excitation power values (though simply denoted by ". . . " in the table, concrete numerical values are put in fact) or patterns of the excitation power values supplied to the quadrupole magnets 9, 13 and the bending magnets 10, 14 in the charged particle beam generator 1 including the synchrotron 12, the quadrupole magnets 18, 19 and 20 and the bending magnet 17 in the first beam transport system 4, the quadrupole magnets 22A, 24A and the steering magnets 7HA, 7VA, 8HA and 8VA in the second beam transport system 5A for the treatment room 2A, the quadrupole magnets 22B, 24B and the steering magnets 7HB, 7VB, 8HB and 8VB in the second beam transport system 5B for the treatment room 2B, the quadrupole magnets 22C, 24C and the steering magnets 7VC, 8HC and 8VC in the second beam transport system 5C for the treatment room 2C, and the quadrupole magnet 28 in the second beam transport system 5D for the treatment room 3, as well as electromotive values (though simply denoted by ". . . " in the table, concrete numerical values are put in fact) of switching power supplies 162-1, 162-2, 162-3 and 162-4 (described later). Note that the magnets are in practice disposed in a larger number in the charged particle beam generator 1 and the respective transport systems, but only main ones of those magnets are shown. Further, in this embodiment, the power supply control table (control command data) is stored in the disk 103 while being divided into two groups (as described later in detail).

The CPU 101 outputs the thus-created control command data to the magnet power supply controller 130. The magnet power supply controller 130 distributes the control command data, inputted from the CPU 101, to the accelerator power supply 140, the beam path power supply 150, the beam switching power supply 160, and the path switching controller 170.

More specifically, the magnet power supply controller 130 distributes, to the accelerator power supply 140, those ones of the created control command data which are related to the quadrupole magnets 9, 13 and the ending magnets 10, 14 in the charged particle beam generator 1. The accelerator power supply 140 comprises, for each magnet, a control unit (so-called ACR, not shown) having the control function to hold a constant current of a desired value, and a power supply unit (not shown) corresponding to each ACR. Each ACR controls the corresponding power supply unit in accordance with the control command data inputted from the magnet power supply controller 130, whereby the magnitudes of respective currents supplied from the power supply units to the quadrupole magnets 9, 13 and the bending magnets 10, 14 are controlled.

Also, the magnet power supply controller 130 distributes, to the beam path power supply 150, those ones of the created control command data other than the data for the charged particle beam generator 1, which are related to the quadrupole magnets 18, 19 and 20 and the bending magnet 17 in the first beam transport system 4, the quadrupole magnets 22A, 24A and the steering magnets 7HA, 7VA, 8HA and 8VA in the second beam transport system 5A for the first treatment room 2A, the quadrupole magnets 22B, 24B and the steering magnets 7HB, 7VB, 8HB and 8VB in the second beam transport system 5B for the second treatment room 2B, the quadrupole magnets 22C, 24C and the steering magnets 7HC, 7VC, 8HC and 8VC in the second beam transport system 5C for the third treatment room 2C, and the quadrupole magnet 28 in the second beam transport system 5D for the fourth treatment room 3. The control command data distributed to the beam path power supply 150 differs depending on the information regarding the treatment room having the top priority, which has been decided by the treatment sequence controller 120, i.e. the information indicating the treatment room number. For example, when the indicated number of the treatment room in which treatment is going to be performed is "No. 1" as mentioned above, the magnet power supply controller 130 distributes, to the beam path power supply 150, the control command data for the quadrupole magnets 18, 22A and 24A, the steering magnets 7HA, 7VA, 8HA and 8VA, and the bending magnet 17, which are disposed in the beam path for introducing the ion beam from the synchrotron 12 to the treatment number indicated by the treatment room number. When the indicated number of the treatment room in which treatment is going to be performed is other than "No. 1", the magnet power supply controller 130 distributes the control command data for the corresponding magnets in a similar way. Like the accelerator power supply 140, the beam path power supply 150 comprises, for each magnet, a control unit (so-called ACR, not shown) having the control function to hold a constant current of a desired value, and a power supply unit (not shown) corresponding to each ACR. Each ACR controls the corresponding power supply unit in accordance with the control command data inputted from the magnet power supply controller 130, whereby the magnitudes of respective currents supplied from the power supply units to the corresponding magnets are controlled.

Further, the magnet power supply controller 130 distributes power supply control data for the switching power supplies 162-1 to 162-4, which is also contained in the created control command data, to the switching power supply 160, and at the same time it outputs treatment room number data (No. 1 in FIG. 4) to the path switching controller 170. In accordance with treatment room number data from the magnet power supply controller 130, the path switching controller 170 performs switching control of various switches (not shown) provided on the switch panel 180. Like the accelerator power supply 140, the switching power supply 160 comprises four control units (so-called ACR, not shown) each having the control function to hold a constant current of a desired value, and four power supply units (i.e., the switching power supplies 162-1 to 162-4 shown in FIG. 5) corresponding to the ACR's. The power supply 162-1 supplies currents to the switching magnet 6A and the bending magnet 21A in the treatment room 2A. The power supply 162-2 supplies a current to the bending magnet 23A therein, the power supply 162-3 supplies a current to the bending magnet 25A therein, and the power supply 162-4 supplies a current to the bending magnet 26A therein. This is similarly applied to the case in which treatment is performed in each of the other treatment rooms 2B, 2C. In other words, each ACR controls the corresponding power supply unit in accordance with the power supply control data inputted from the magnet power supply controller 130, whereby the magnitudes of respective currents supplied from the power supply units to the corresponding magnets are controlled. Furthermore, the path switching controller 170 performs switching control of the various switches provided on the switch panel 180 in accordance with the treatment room number data, whereby the current supply destination to which the current is supplied from each power supply (i.e., the treatment room number) is controlled.

When the settings of excitation currents for the respective magnets, which are performed by the accelerator power supply 140, the beam path power supply 150, the beam switching power supply 160, and the path switching controller 170, have completed in such a way, the magnet power supply controller 130 outputs a signal for displaying the completion of the settings to the CPU 101 in the central control unit 100. Correspondingly, the CPU 101 outputs, to the display 39 of the operator console 37, a signal indicating that the final setup on the machine side has completed. In response to such a display signal, the display 39 presents display for indicating the completion of the final setup on the machine side (i.e., display for confirming the final intent to start the irradiation). Then, when the irradiation instruction switch (or button) 42 is depressed by an authorized person, for example, a doctor (an operator is also allowed overseas, but in Japan the authorized person is statutorily limited to only a doctor from the viewpoints of safety and humanity), a corresponding irradiation start instruction signal is inputted to the CPU 101 in the central control unit 100.

Then, the central control unit 100 outputs an emission instruction signal and an acceleration instruction signal, respectively, to the linac 11 and the above-mentioned RF cavity of the synchrotron 12. Responsively, the ion beam emitted from the charged particle beam generator 1 is accelerated in the synchrotron 12, and the ion beam extracted from the synchrotron 12 is transported to the first beam transport system 4. Further, the ion beam is introduced to one of the second beam transport systems 5A to 5D corresponding to one of the treatment rooms 2A to 2C and 3 in which the patient as an irradiation target is present. The ion beam is then irradiated to the diseased part in the body of the patient 30A in an optimum form, as per the treatment planning, through one of the irradiation apparatuses 15A to 15C and 16 in the treatment rooms 2A to 2C and 3.

In the particle therapy system having the basic construction described above, the most important feature of the present invention resides in that, in the central control unit 100, the control command data listed in the power supply control table of FIG. 5 is stored in the disk 103 while being divided into two groups.

Figure 6:
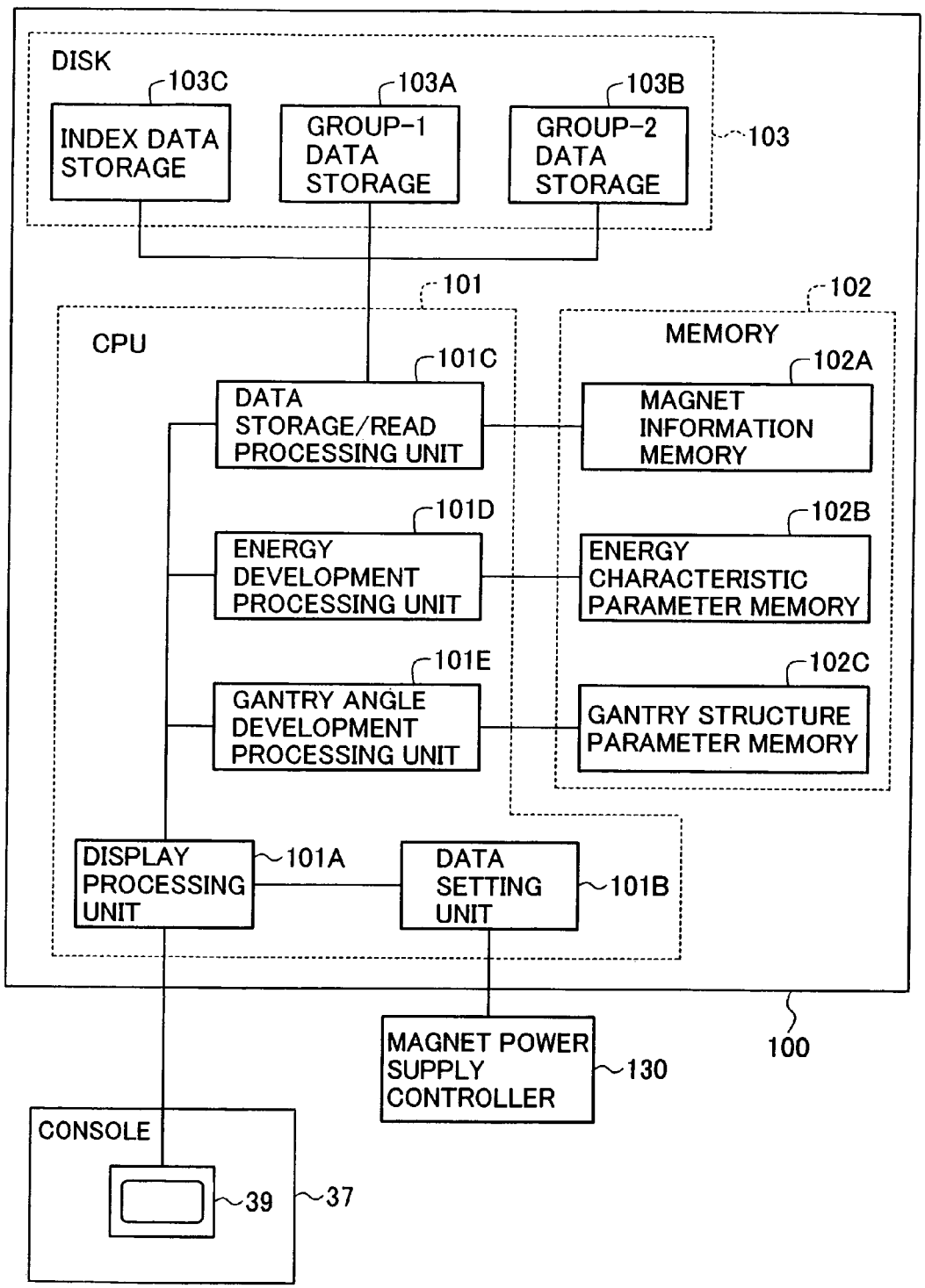
FIG. 6 is a functional block diagram showing those ones of the functions of the central control unit which are related to a process for storing control command data.

FIG. 6 is a functional block diagram showing those ones of the functions of the central control unit 100 which are related to a process for storing the control command data. As shown in FIG. 6, the disk 103 has a group-1 data storage (first command value storing means) 103A for storing control command data belonging to a group 1 (hereinafter referred to as "group-1 data"; first command value group) which is contained in the control command data shown, by way of example, in FIG. 5, a group-2 data storage (second command value storing means) 103B for storing control command data belonging to a group 2 (hereinafter referred to as "group-2 data"; second command value group) which is also contained in the control command data, and an index data storage (index information storing means) 103C for storing index data (index information) to make the group-1 data and the group-2 data correspondent to each other. Also, a memory 102 includes a magnet information memory 102A in which magnet information required for a data storage/read processing unit 101C (described later) to write and read data is stored, an energy characteristic parameter memory 102B in which an energy development algorithm is stored, and a gantry structure parameter memory 102C in which a gantry angle development algorithm is stored. Further, the CPU 101 includes a display processing unit 101A for processing display information displayed on the display 39 of the console 37; a data setting unit 101B for setting the control command data outputted to the magnet power supply controller 130, the data storage/read processing unit (reading means) 101C for executing write and read of data in and from the group-1 data storage 103A, the group-2 data storage 103B, and the index data storage 103C; an energy development processing unit (energy development computing means) 101D for newly computing the group-1 data and the group-2 data depending on the beam energy by using the energy development algorithm stored in the energy characteristic parameter memory 102B; and a gantry angle development processing unit (angle development computing means) 101E for newly computing the group-2 data depending on the rotation angle of the rotating gantry by using the gantry angle development algorithm stored in the gantry structure parameter memory 102C. The gantry angle development algorithm stored in the gantry structure parameter memory 102C means parameters of the type empirically determined from the structure and characteristics of the rotating gantry. Also, the energy development algorithm stored in the energy characteristic parameter memory 102B means parameters of the type empirically determined from the structures of the ion source (not shown), the pre-stage charged particle beam generator 11 and the synchrotron 12, and from overall characteristics of the charged particle beam generator 1.

FIG. 5 shows classification into the group-1 data stored in the group-1 data storage 103A and the group-2 data stored in the group-1 data storage 103B. In this embodiment, as shown in FIG. 5, the control command data for the steering magnets 7VA-7VC, 7HA-7HC, 8VA-8VC and 8HA-8HC disposed in the gantry system is classified into the group-2 data, and the control command data for the other magnets is classified into the group-1 data. The control command data for the steering magnets 7VA-7VC, 7HA-7HC, 8VA-8VC and 8HA-8HC is command data depending on the rotation angle of the rotating gantry. This is because, when the rotating drum 50 of the rotating gantry is rotated, the beam path is distorted by the weight of the rotating drum 50 itself and the beam position must be finely adjusted with the steering magnets 7VA-7VC, 7HA-7HC, 8VA-8VC and 8HA-8HC. The control command data for the other magnets is command data not depending on the gantry angle.

The index data stored in the index data storage 103C is added to one set of control command data (i.e., command data for all the magnets corresponding to each level of beam energy shown in FIG. 5) in a one-to-one relation. FIG. 7 is an illustration showing one example of the index data displayed on the display 39 of the console 37. As shown in FIG. 7, the index data includes the file name of the control command data, the name of a person having prepared the data, and the name of a person having approved it. From the information displayed as the index data, the operator can easily confirm the contents of the control command data. The index data further includes the beam energy, the course (i.e., the treatment room number; courses 1, 2, 3 and 4 corresponding respectively to the treatment rooms 2A, 2B, 2C and 3), the beam intensity (corresponding to the irradiation dose in the treatment planning data), and the gantry angle. Those items are parameters required to specify the beam. It is needles to say that the index data may include other parameters for giving the operator more comprehensive understanding.

Figure 8:
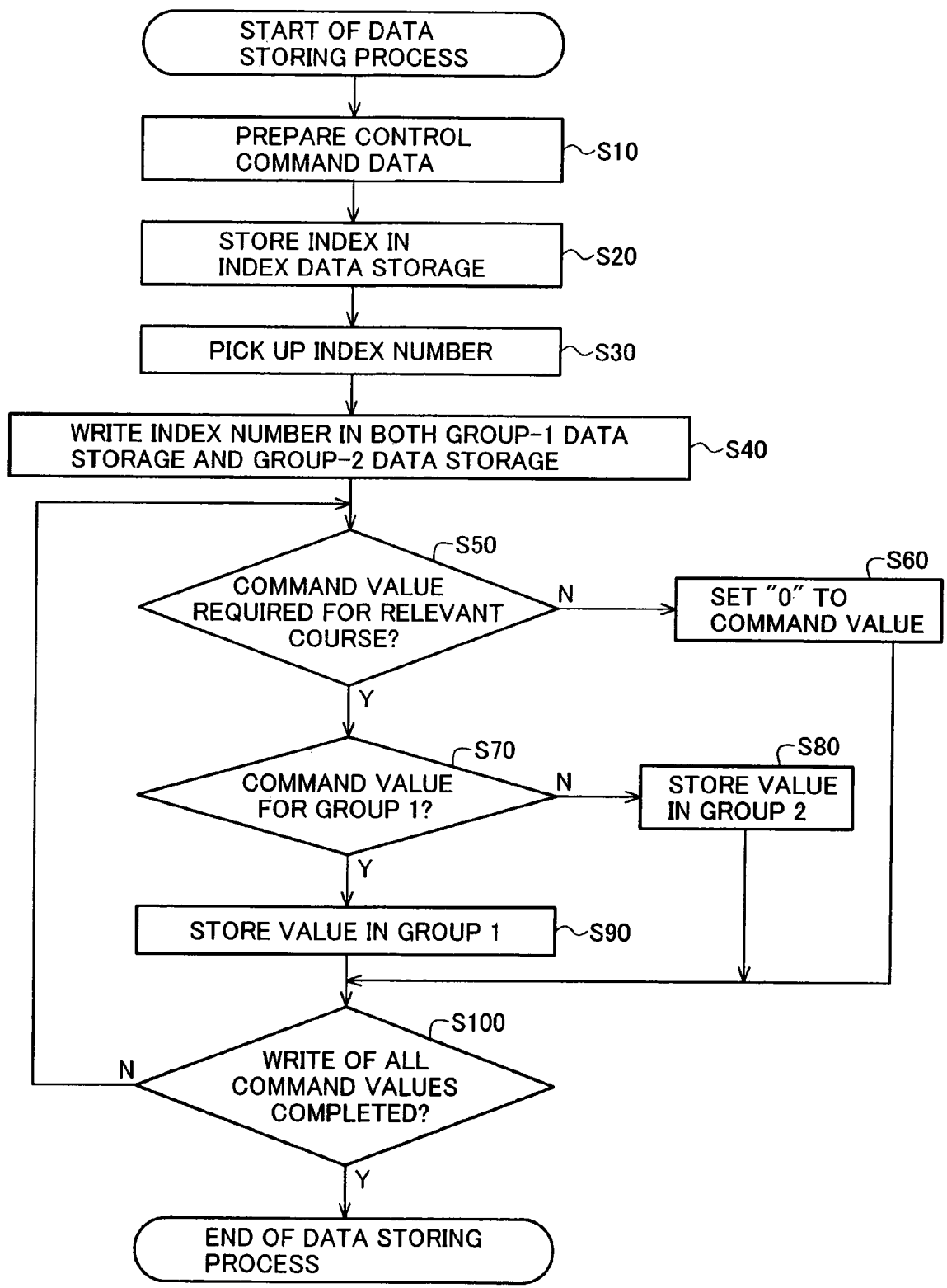
FIG. 8 is a flowchart showing a flow of the process for storing the control command data to prepare the power supply control table in the disk disposed in the central control unit.

FIG. 8 is a flowchart showing a flow of the process for storing the control command data to prepare the power supply control table in the disk 103 disposed in the central control unit 100.

First, in step S10, control command data is prepared by the operator adjusting the control command data applied to the respective magnets while actually irradiating the beam. Based on the prepared control command data the energy development processing unit 101D computes control command data (as described later in more detail) by using the energy development algorithm stored in the energy characteristic parameter memory 102B. Further, the gantry angle development processing unit 101E computes control command data (as described later in more detail) by using the gantry angle development algorithm stored in the gantry structure parameter memory 102C.

In next step S20, the operator inputs parameters from the console 37 while looking at an entry screen displayed on the display 39, by way of example, as shown in FIG. 7, thereby preparing index data regarding those items of the control command data prepared in step S10 which are to be stored. The prepared index data is stored in the index data storage 103C through the data storage/read processing unit 101C.

In next step S30, the data storage/read processing unit 101C picks up and defines an index number corresponding to the index data prepared in step S20.

In next step S40, the data storage/read processing unit 101C stores the index number picked up in step S30 in each of the group-1 data storage 103A and the group-2 data storage 103B. When the group-1 data and the group-2 data are read by the data storage/read processing unit 101C, the index number is used as a key for specifying the corresponding group-1 data and group-2 data. Stated another way, the index number stored in each of the group-1 data storage 103A and the group-2 data storage 103B serves to make the group-1 data and the group-2 data belonging to the same set of control command data correspondent to each other.

In next step S50, by using the parameters stored in the magnet information memory 102A, the data storage/read processing unit 101C determines on the basis of one item by one item whether the prepared control command data is command data required for the relevant course. If the command data is not required for the relevant course, the determination is not satisfied and the command data is set to "0" in next step S60, followed by proceeding to step S100 described later. In practice, for example, when treatment is performed in the treatment room 2A, the command data for the magnets downstream of the quadrupole magnet 19 is set to "0". If the command data is required for the relevant course, the determination is satisfied, followed by proceeding to step S70.

In next step S70, by using the parameters stored in the magnet information memory 102A, the data storage/read processing unit 101C determines whether the prepared control command data belongs to the group-1 data. In practice, it is determined whether the magnets to which the command data is to be outputted are the steering magnets 7VA-7VC, 7HA-7HC, 8VA-8VC and 8HA-8HC. If the magnets to which the command data is to be outputted are those steering magnets, the determination is not satisfied, followed by proceeding to step S80 in which the command data is classified as group-2 data and stored in the group-2 data storage 103B. Then, the control flow shifts to step 100 (described later). If the magnets to which the command data is to be outputted are not those steering magnets, the determination is satisfied, followed by proceeding to step S90 in which the command data is classified as group-1 data and stored in the group-1 data storage 103A. Then, the control flow shifts to step S100.

In step S100, the data storage/read processing unit 101C determines whether the processing of steps S50 to S90 has been completed for all items of the prepared control command data. If not yet completed, the control flow returns to step S50 to repeat the processing of steps S50 to S90. If all items of the necessary command data have been stored, the determination is satisfied and the control flow comes to an end.

Figure 9:
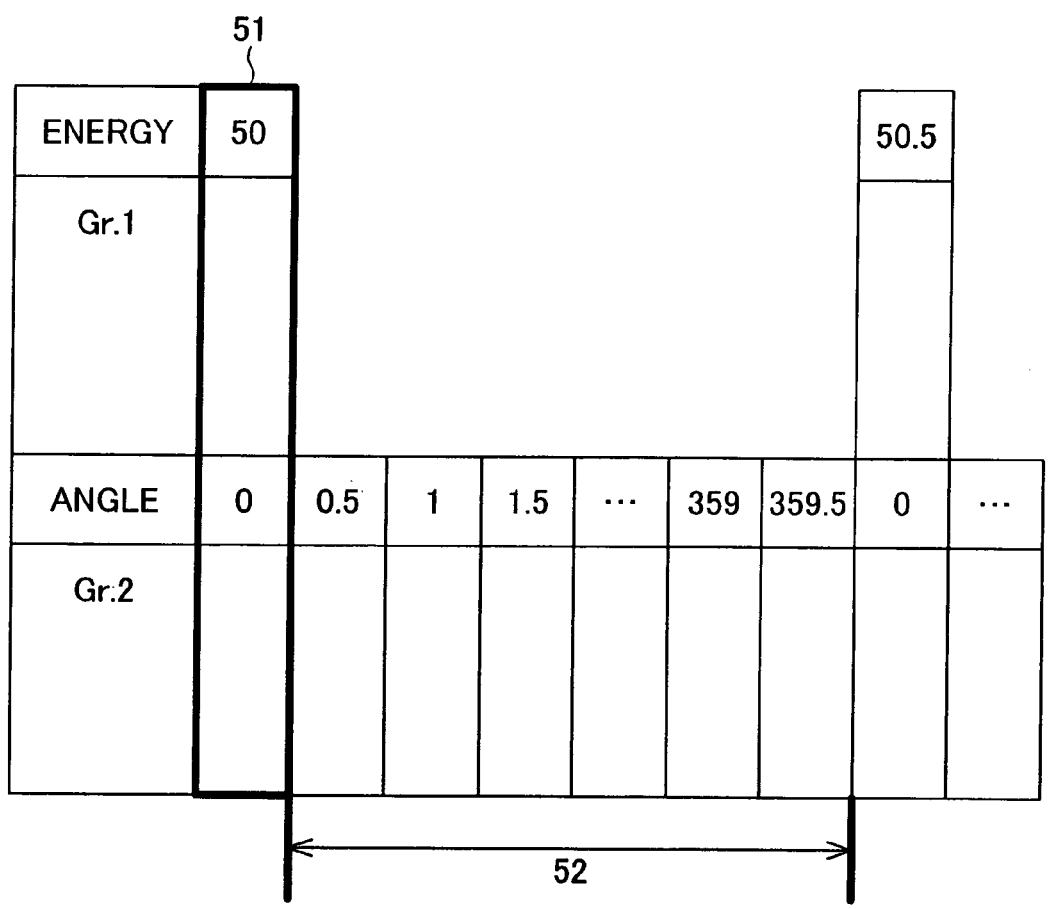
FIG. 9 is a table showing one example of control command data newly computed in a gantry angle development processing unit by using a gantry angle development algorithm.

FIG. 9 is a table showing one example of the control command data newly computed in the gantry angle development processing unit 101E by using the gantry angle development algorithm.

As mentioned above, the operator first prepares control command data by adjusting control command data applied to the respective magnets while actually irradiating the beam. It is here assumed that the control command data indicated by 51 in FIG. 9, i.e., the control command data representing the beam energy of 50 MeV, the beam intensity of 100%, the course 1 (treatment room 2A), and the gantry angle of 0 degree, has been prepared by the operator. Based on the control command data 51 thus prepared, the gantry angle development processing unit 101E automatically computes the group-2 data depending on the gantry angle (e.g., the group-2 data covering the gantry angle in the range of 0.5 to 359.5 degrees in units of 0.5 degree) by using the gantry development algorithm. An area indicated by a double-headed arrow 52 in FIG. 9 represents the group-2 data newly prepared at this time. The newly prepared group-2 data is sent to the data storage/read processing unit 101C and is stored in the group-2 data storage 103B in accordance with the flowchart shown in FIG. 8. Then, the operator newly prepares index data with, e.g., entry from the console 37, and the prepared index data is stored in the index data storage 103C through the data storage/read processing unit 101C. In addition, an index number is also defined. Since the group-1 data does not depend on the gantry angle as described above, the group-1 data in the control command data 51 can be used in common to all of the group-2 data newly computed.

Figure 10:
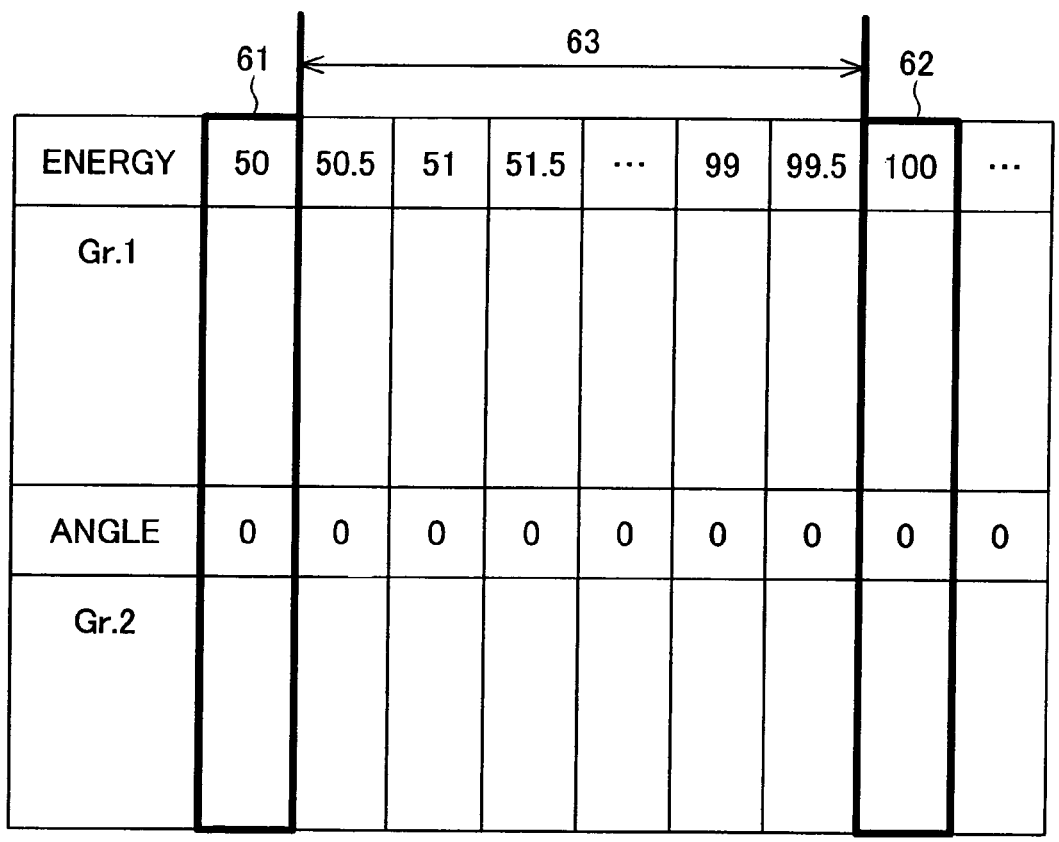
FIG. 10 is a table showing one example of control command data newly computed in an energy development processing unit by using an energy development algorithm.

On the other hand, FIG. 10 is a table showing one example of the control command data newly computed in the energy development processing unit 101D by using the energy development algorithm.

As mentioned above, the operator first prepares control command data by adjusting the control command data applied to the respective magnets while actually irradiating the beam. It is here assumed that the control command data indicated by 61, 62 in FIG. 10, i.e., the control command data representing the beam energy of 50 MeV, the beam intensity of 100%, the course 1 (treatment room 2A) and the gantry angle of 0 degree, and the control command data representing the beam energy of 100 MeV, the beam intensity of 100%, the course 1 (treatment room 2A) and the gantry angle of 0 degree, have been prepared by the operator. Based on the control command data 61, 62 thus prepared, the energy development processing unit 101D automatically computes the group-1 data and the group-2 data depending on the beam energy (e.g., the group-1 data and the group-2 data covering the beam energy in the range of 50.5 to 100 MeV in units of 0.5 MeV) by using the energy development algorithm. An area indicated by a double-headed arrow 63 in FIG. 10 represents the group-1 data and the group-2 data both newly prepared at this time. The newly prepared group-1 data and group-2 data are sent to the data storage/read processing unit 101C and are stored respectively in the group-1 data storage 103A and the group-2 data storage 103B in accordance with the flowchart shown in FIG. 8. Then, the operator newly prepares index data with, e.g., entry from the console 37, and the prepared index data is stored in the index data storage 103C through the data storage/read processing unit 101C. In addition, an index number is also defined. In this way, the power supply control table is prepared and stored in the disk 103 disposed in the central control unit 100.

The operation of the particle therapy system of this embodiment, having the above-described construction, will be described below with reference to FIG. 11. FIG. 11 a time chart showing a flow of the operation and control over time in the particle therapy system according to this embodiment.

The CPU 101 in the central control unit 100 reads, from the storage 110, the treatment planning data regarding the patient who is going to take the irradiation treatment, and outputs the necessary data to the respective controllers via the irradiation controller 40. The respective controllers perform the adjustment of the gantry angle, the setting of the irradiation apparatus 15, the positioning of the treatment couch 29A, etc. When those patient setups are completed, the operator depresses the setup completion switch 38 on the operator console 37, whereupon the patient ready signal is outputted to the treatment sequence controller 120. The treatment sequence controller 120 decides the sequence of treatments to be performed in the treatment rooms 2A, 2B, 2C and 3 in accordance with the input sequence of the patient ready signals. A treatment room signal indicating the decided treatment sequence is inputted to the CPU 101 in the central control unit 100. By using the thus inputted treatment room signal (i.e., beam course information) and the parameters (such as the irradiation energy, the irradiation dose (beam intensity), and the gantry angle) which are contained in the treatment planning data and are required to specify the beam, the CPU 101 creates control command data for supply of excitation power to the respective magnets based on the power supply control table that is stored in the disk 103 disposed in the central control unit 100. The control command data thus prepared is outputted to the magnet power supply controller 130 and then distributed from the magnet power supply controller 130 to the accelerator power supply 140, the beam path power supply 150, the beam switching power supply 160, and the path switching controller 170. When those power supplies 140, 150 and 160 and the path switching controller 170 have completed the settings of excitation currents supplied to the respective magnets, the magnet power supply controller 130 outputs a signal indicating the completion of the equipment settings to the CPU 101 in the central control unit 100, whereupon the CPU 101 outputs a signal indicating the completion of the final setup on the machine side to the display 39 of the operator console 37. Correspondingly, the display 39 presents display for indicating the completion of the final setup on the machine side. Then, when the irradiation instruction switch 42 is depressed by, e.g., a doctor, a corresponding irradiation start instruction signal is inputted to the CPU 101 in the central control unit 100. In response to the irradiation start instruction signal, the CPU 101 outputs an emission instruction signal and an acceleration instruction signal, respectively, to the linac 11 and the above-mentioned RF cavity of the synchrotron 12. As a result, the ion beam from the charged particle beam generator 1 is extracted and irradiated to the diseased part in the body of the patient 30A through the irradiation apparatus in the relevant treatment room.

As shown in FIG. 11, a treatment time from the patient setup in each treatment room to the end of the beam irradiation is divided primarily into a patient setup time (i.e., a time required to complete the setup for the patient) T1, a beam setup time T2, and a beam irradiation time T3. In the beam setup time T2, a time required for creating the control command data occupies a large part though it is shown short in FIG. 11 for easier understanding of a signal flow.

The particle therapy system of this embodiment having been described above in detail operates with the following advantages.

In this embodiment, the control command data is stored while being classified into two groups such that, of the respective magnets disposed in the charged particle beam generator 1 and the beam transport systems 4, 5A, 5B, 5C and 5D for transporting the ion beam extracted from the charged particle beam generator 1 to the irradiation apparatuses 15A-15C and 16, the control command data for the steering magnets 7HA-7HC, 7VA-7VC, 8HA-8HC and 8VA-8VC is classified into the group-2 data, and the control command data for the other magnets is classified into the group-1 data. Classifying, as another group, only the control command data depending on the gantry angle is advantageous in that, as to the control command data for the beam types differing only in the angle of the rotating gantry, it is just required to store the group-2 data alone in the group-2 data storage 103B, whereas the group-1 data can be used in common. The number of the steering magnets disposed in the gantry transport system, which belong to the group-2 data, is several (four in this embodiment) at maximum in each treatment room (i.e., per course). On the other hand, though depending on the number of courses, the number of the other magnets belonging to the group-1 data is usually about 30 to 150 (FIG. 5 shows only the main magnets and hence includes a relatively small number of magnets). With this embodiment, therefore, as to the control command data for the beam types differing only in the angle of the rotating gantry, the group-1 data for about 30 to 150 magnets can be used in common, whereas it is just required to store the group-2 data alone for several magnets at maximum depending on the gantry angle. Accordingly, the amount of the command data to be stored can be greatly reduced in comparison with the known system in which the control command data for the respective magnets is all simply stored as it is. As a result, it is possible to cut a search time required for specifying, from among the stored control command data, the necessary command data corresponding to the requested beam type. In other words, the time required for creating the control command data, shown in FIG. 11, can be shortened, whereby the beam setup time T2 can be shortened. Usually, in a particle therapy system including a plurality of treatment rooms as in this embodiment, during a period in which the beam setup and the beam irradiation are performed in one treatment room, a next treatment room completes a patient setup and comes into a standby state. Therefore, as soon as the irradiation has completed in one treatment room, the beam setup for the next treatment room is performed at once. Accordingly, if the beam setup time T2 is prolonged, the standby time of the next treatment room is prolonged and treatment efficiency is reduced correspondingly. In contrast, with this embodiment, since the beam setup time T2 can be cut, the number of patients treated in one treatment room per unit time can be increased. Moreover, since the amount of the command data to be stored can be greatly reduced as described above, it is possible to reduce the resources (such as a hard disk or a CD-ROM) necessary for storing the control command data, to improve convenience in handling of data, and to cut the cost.

Also, with this embodiment, the energy development processing unit 101D and the gantry angle development processing unit 101E automatically compute and store the control command data depending on the beam energy and the gantry angle, respectively. Therefore, whatever beam energy and whatever gantry angle are requested from any of the treatment rooms, the beam setting can be automatically performed in response to the request, and the range within which the central control unit 100 is able to automatically perform the beam setting can be drastically enlarged.

Further, with this embodiment, the index data is added to one set of control command data in a one-to-one relation, and the index number corresponding to the index data is defined and stored when the control command data is classified into the group-1 data and the group-2 data. Based on the index data, the operator can easily confirm the contents of the control command data, and can write and read the control command data as one set without being aware of the fact that the control command data is stored in two classified groups. In other words, lowering of convenience in handling of data can be avoided which is otherwise caused with classification of the control command data into two groups. Further, when reading the command data from the two groups, the defined index number is used as a key for specifying both the group-1 data and the group-2 data corresponding to it. Therefore, the group-1 data and the group-2 data can be avoided from being read in a false combination.

While the beam irradiation method in the irradiation apparatus is not limited to a particular one in the above-described one embodiment of the present invention, the present invention is likewise applicable to, e.g., a particle therapy system including an irradiation apparatus of the type irradiating an ion beam while automatically changing beam energy to plural levels (i.e., the energy scanning type). In such a case, plural sets of the control command data corresponding to the plural energy levels must be selected from the power supply control table stored in the disk 103 in response to the beam request from each treatment room. Stated another way, in that case, the search for the control command data executed in the above-described one embodiment requires to be made plural times corresponding to the plural energy levels. It is hence possible to more effectively utilize the advantage of the present invention that the number of patients treated in one treatment room per unit time by cutting the search time.

While the above-described one embodiment of the present invention is applied to the particle therapy system including the synchrotron, the present invention can also be applied to a particle therapy system including a cyclotron.

What is claimed is:

1. A particle therapy system comprising:
a charged particle beam generator for generating a charged particle beam;
an irradiation apparatus for irradiating the charged particle beam extracted from said charged particle beam generator to an irradiation target;
a rotating gantry including said irradiation apparatus and installed rotatably;
a beam transport system for transporting the charged particle beam extracted from said charged particle beam generator to said irradiation apparatus, said beam transport system including a gantry portion located in said rotating gantry; and
a control unit for controlling part of magnets disposed in said gantry portion of said beam transport system by using first command values of a first command value group depending on a rotation angle of said rotating gantry in a group of command values stored in storing means to command excitation currents for magnets disposed in said charged particle beam generator and said beam transport system, and controlling said magnets disposed in said charged particle beam generator and the magnets disposed in said beam transport system other than said part of magnets disposed in said gantry portion by using second command values of a second command value group not depending on the rotation angle of said rotating gantry in said group of command values stored in said storing means.

2. A particle therapy system comprising:
a charged particle beam generator for generating a charged particle beam;
an irradiation apparatus for irradiating the charged particle beam extracted from said charged particle beam generator to an irradiation target;
a rotating gantry including said irradiation apparatus and installed rotatably;
a beam transport system for transporting the charged particle beam extracted from said charged particle beam generator to said irradiation apparatus, said beam transport system including a gantry portion located in said rotating gantry; and
a control unit for controlling steering magnets disposed in said gantry portion of said beam transport system by using first command values of a first command value group in a group of command values stored in storing means to command excitation currents for magnets disposed in said charged particle beam generator and said beam transport system, and controlling said magnets disposed in said charged particle beam generator and the magnets disposed in said beam transport system other than said steering magnets by using second command values of a second command value group in said group of command values stored in said storing means.

3. A particle therapy system according to claim 1 or 2, further comprising angle development computing means for computing the first command value group depending on the rotation angle of said rotating gantry.

4. A particle therapy system according to claim 1 or 2, further comprising energy development computing means for computing the first and second command value groups depending on energy of the charged particle beam extracted from said charged particle beam generator.

5. A particle therapy system according to claim 1 or 2, said storing means includes first command value storing means for storing the first command value group, second command value storing means for storing the second command value group, and index information storing means for storing index information to make the first command value group and the second command value group correspondent to each other.

6. A particle therapy system according to claim 3, said storing means includes first command value storing means for storing the first command value group, second command value storing means for storing the second command value group, and index information storing means for storing index information to make the first command value group and the second command value group correspondent to each other.

7. A particle therapy system according to claim 5, said control unit includes reading means for reading the first command value group and the second command value group, which are made correspondent to each other, out of said first command value storing means and said second command value storing means by using the index information read out of said index information storing means.

8. A particle therapy system according to claim 1, wherein said part of magnets disposed in said gantry portion of said beam transport system comprises steering magnets of which the excitation currents are controlled by said control unit based on said first command values.

9. A particle therapy system according to claim 2, further comprising said storing means in which said first and second command value groups are stored.

10. A particle therapy system according to claim 8 or 9, further comprising angle development computing means for computing the first command value group depending on the rotation angle of said rotating gantry.

11. A particle therapy system according to claim 8 or 9, further comprising energy development computing means for computing the first and second command value groups depending on energy of the charged particle beam extracted from said charged particle beam generator.

12. A particle therapy system according to claim 8 or 9, said storing means includes first command value storing means for storing the first command value group, second command value storing means for storing the second command value group, and index information storing means for storing index information to make the first command value group and the second command value group correspondent to each other.

13. A particle therapy system according to claim 1, further comprising said storing means in which said first and second command value groups are stored.

14. A particle therapy system according to claim 2, wherein said storing means stores said first command value group as a command value group depending on a rotation angle of said rotating gantry and stores said second command value group as a command value group not depending on a rotation angle of said rotating gantry.

* * * * *

UNITED STATES PATENT AND TRADEMARK OFFICE
CERTIFICATE OF CORRECTION

PATENT NO.       : 7,586,112 B2
APPLICATION NO.  : 11/339842
DATED            : September 8, 2009
INVENTOR(S)      : Chiba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 569 days.

Signed and Sealed this

Fourteenth Day of September, 2010

David J. Kappos
*Director of the United States Patent and Trademark Office*